(12) United States Patent
Zaleski

(10) Patent No.: US 6,956,572 B2
(45) Date of Patent: Oct. 18, 2005

(54) PATIENT MEDICAL PARAMETER USER INTERFACE SYSTEM

(75) Inventor: John R. Zaleski, West Brandywine, PA (US)

(73) Assignee: Siemens Medical Solutions Health Services Corporation, Malvern, PA (US)

( * ) Notice: Subject to any disclaimer, the term of this patent is extended or adjusted under 35 U.S.C. 154(b) by 66 days.

(21) Appl. No.: 10/616,219

(22) Filed: Jul. 8, 2003

(65) Prior Publication Data

US 2004/0158132 A1 Aug. 12, 2004

Related U.S. Application Data

(60) Provisional application No. 60/446,313, filed on Feb. 10, 2003.

(51) Int. Cl.[7] .............................. G09G 5/22; A61B 5/00
(52) U.S. Cl. .................................... 345/440.2; 600/300
(58) Field of Search ............................ 345/440, 440.1, 345/440.2, 700, 762, 764, 883; 600/300, 301

(56) References Cited

U.S. PATENT DOCUMENTS

| | | | |
|---|---|---|---|
| 5,482,050 A | | 1/1996 | Smokoff et al. ............ 128/710 |
| 5,915,379 A | * | 6/1999 | Wallace et al. ........ 128/204.21 |
| 6,095,984 A | | 8/2000 | Amano et al. |
| 6,174,283 B1 | | 1/2001 | Nevo et al. ................. 600/301 |
| 6,188,407 B1 | | 2/2001 | Smith et al. ................. 345/353 |
| 6,269,812 B1 | | 8/2001 | Wallace et al. ........ 128/205.23 |
| 6,287,452 B1 | | 9/2001 | Allen et al. |
| 6,369,838 B1 | | 4/2002 | Wallace et al. ............. 345/810 |
| 6,429,869 B1 | * | 8/2002 | Kamakura et al. ....... 345/440.2 |
| 2002/0015034 A1 | | 2/2002 | Malmborg et al. .......... 345/204 |
| 2002/0077863 A1 | | 6/2002 | Rutledge et al. ............... 705/3 |
| 2002/0082867 A1 | | 6/2002 | MacCarter et al. ............ 705/2 |
| 2002/0183976 A1 | | 12/2002 | Pearce ........................ 702/188 |
| 2003/0037786 A1 | * | 2/2003 | Biondi et al. .......... 128/204.21 |
| 2003/0092974 A1 | | 5/2003 | Santoso et al. ............. 600/300 |
| 2003/0095147 A1 | | 5/2003 | Daw .......................... 345/771 |
| 2004/0116804 A1 | * | 6/2004 | Mostafavi ................... 600/428 |

FOREIGN PATENT DOCUMENTS

DE 198 44 918 A1 9/1998

* cited by examiner

*Primary Examiner*—Matthew Luu
(74) *Attorney, Agent, or Firm*—Alexander J. Burke, Esq.

(57) ABSTRACT

A user interface enables a critical care clinician (such as a respiratory therapist, nurse, resident, or attending physician) to quickly ascertain a patient condition as part of a patient care management procedure. A system according to invention principles comprises a user interface display providing a quick and convenient way to display key vital parameters and their acceptable ranges within the immediate eye-span of a clinician. A system provides a user interface presenting patient medical parameter data, and includes an acquisition processor for acquiring, from a patient monitoring device, data representing a patient parameter. The system includes a processor for initiating generation of data representing at least one display image including, (a) a current value of a patient parameter and (b) a sliding bar representation of the patient parameter current value together with a range indicator for graphically indicating whether the current value is outside of a user determined range.

21 Claims, 8 Drawing Sheets

|   | Vascular |   | Respiratory |   | Laboratory |
|---|---|---|---|---|---|
| ☑ | Pulse | ☑ | Resp Rate | ☐ | Hemoglobin |
| ☐ | Cardiac Index | ☑ | Tidal Volume | ☐ | K |
| ☑ | Cardiac Output | ☐ | Minute Volume | ☐ | Ca |
| ☑ | O2 Saturation | ☑ | PEEP | ☐ | SaO2 |
| ☑ | Core Temp | ☑ | RSBI | ☐ | PO2 |
| ☐ | PAP | ☐ | IMV Level | ☐ | PCO2 |
| ☐ | CVP | ☐ | Dyn. Compl. | ☐ | pH |
| ☐ |  | ☐ |  | ☐ |  |
| ☐ |  | ☐ |  | ☐ |  |

Selected Parameters

Pulse Cardiac
Output C2
Saturation
Temperature RR
TVe Cardiac Index
Cardiac Index Mass (kg) 53
Height (cm) 145

PATIENT MEDICAL PARAMETER USER INTERFACE SYSTEM

This is a non-provisional application of provisional application Ser. No. 60/446,313 by J. R. Zaleski filed Feb. 10, 2003.

FIELD OF THE INVENTION

This invention is related to adaptively processing and displaying of medical information, and more particularly to processing and displaying patient medical data for user configurable display in a network environment.

BACKGROUND OF THE INVENTION

Patient medical parameter data is acquired, collated, stored and displayed for use in providing patient clinical care in hospitals, clinics, and other healthcare delivery settings. Patient medical parameter data may include vital signs ventilator information, infusion pump data associated with fluid delivery and other data. Such patient medical parameter data is typically displayed on a patient monitoring device screen in a trend indicative chart with a time axis. This type of chart is commonly termed a Flowsheet which is an electronic chronological chart of patient information that substitutes for a paper vital sign chart. A patient monitoring device is usually located at a patient bedside or nursing station in a hospital ward or in an intensive care, surgical or other location and may be connected to a network such as the Internet, a LAN, a WAN or an intra-net for acquiring patient parameter data from local sources (e.g., patient attached sensors) or remote sources (e.g., a remotely stored electronic patient record).

Existing patient parameter information display and Flowsheet systems fail to present patient vital parameter information in a manner that enables a user to quickly and accurately identify abnormal conditions that may require immediate intervention. Though known systems enable comparisons to be made between normal and abnormal parameters, these system fail to provide a user friendly presentation format enabling a user to quickly, efficiently and comprehensively identify abnormal or other conditions within a restricted image presentation. A system according to invention principles addresses these limitations and derivative problems.

SUMMARY OF THE INVENTION

A system according to invention principles comprises a user interface display providing a quick and convenient way to view key vital parameters and their acceptable ranges within the immediate eye-span of a clinician. A system provides a user interface presenting patient medical parameter data, and includes an acquisition processor for acquiring, from a patient monitoring device, data representing a patient parameter. The system includes a processor for initiating generation of data representing at least one display image including, (a) a current value of a patient parameter and (b) a sliding bar representation of the patient parameter current value together with a range indicator for graphically indicating whether the current value is outside of a user defined range.

BRIEF DESCRIPTION OF THE DRAWINGS

In the drawing:

FIGS. 4 and 5 show user interface display images supporting a user in configuring a user interface display, according to the present invention.

DETAILED DESCRIPTION OF INVENTION

The inventors have advantageously recognized that it is desirable to provide a user interface providing a display of key patient vital parameters and their acceptable ranges within the immediate eye-span of a clinician. This makes it easier for the user to quickly identify a parameter deviating from a normal range (without having to sift through lists of values within an Electronic Patient Record (EPR) or a flowsheet) while at the same time seeing an immediate comparison between normal and abnormal values as well as between current and preceding values. The user interface includes a user view, set up pages, database, and associated functions to present a dynamic, substantially real-time visual display of key patient state parameters. A visual display advantageously provides a parameter display in the form of an analog bar identifying a parameter value by an indicator position along a bar and also showing normal patient values together with levels of deviation from the standard patient parameter values.

Figure 1:
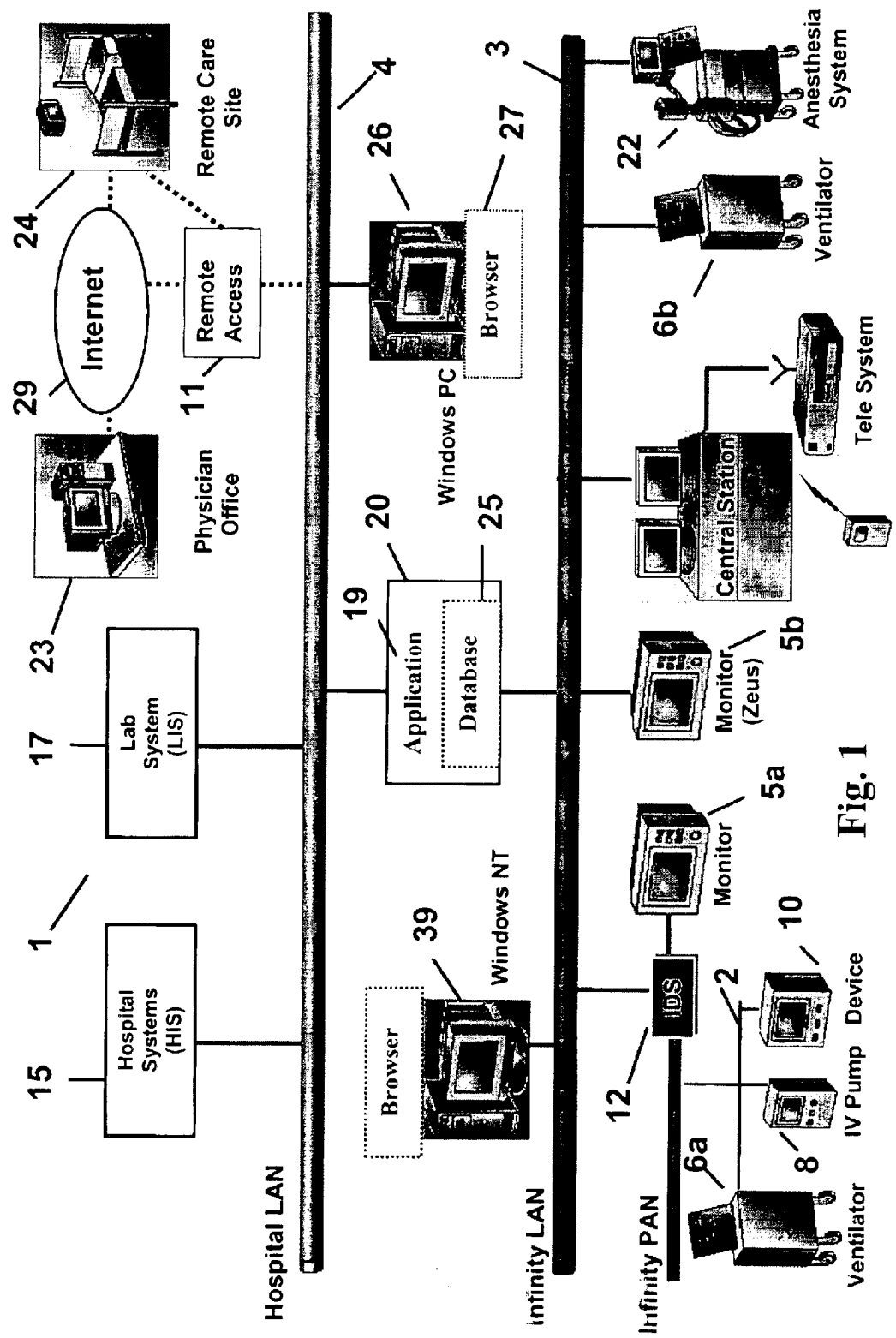
FIG. 1 is a block diagram of a communication network with various devices, according to the principles of the invention.

FIG. 1 is an exemplary block diagram of a communication network incorporating server 20 hosting executable application 19 providing a user interface display of patient parameters according to invention principles. The user interface system displays different types of parameters associated with, for example, Intra-Venous fluids, drip administered medications, blood products, blood pressure, ventilation, vital signs, blood oxygen concentration, and infusion pump fluid delivery. Executable application 19 in other embodiments may be resident in another processing device in any part of the network shown in FIG. 1. Communication network 1 (FIG. 1) is represented by an IP (Internet Protocol) compatible network with a hierarchy of local area and wide area networks interconnected together. It is to be noted that although the present exemplary hospital or medical network is an IP compatible network, other types of networks such as, but not limited to optical or wireless networks, using other computing protocols such as, but not limited to, for example, X.25, frame relay, IBM SNA etc., may also be used, as one skilled in the art can readily appreciate. In addition, although the exemplary network described is a hierarchical network, this is not required by the present invention. Any type of network architecture that provides communication connectivity among the devices on the network may be used.

As shown In FIG. 1, the first level of the exemplary hierarchical network 1 comprises a Medical Interface Information Bus (MIB) 2. A MIB is a well-known medical industry standard for locally connecting medical devices together. As shown in FIG. 1, MIB 2 is typically used to interconnect medical devices in a care unit such as a patient's room within a nursing station to administer care to a particular patient and to monitor the particular patient.

Various medical devices may be connected via MIB 2; examples shown in FIG. 1 comprise a ventilator 6a, IV (Intravenous) Pump 8 or other medical equipment 10. MIB 2 is typically connected to a second level LAN network 3 through an Interface Docking Station (IDS) device 12, for interfacing to Ethernet-compatible LAN network 3. The LAN 3 may be for example, an Infinity LAN, marketed by Siemens Medical System. This higher-level LAN 3 is typically, though not necessarily, used by other care units such as a particular department within a hospital, for instance an intensive care unit or surgery unit, etc., depending on the size of the organization.

Although not shown in FIG. 1, more than one MIB may be connected to the second level LAN 3, so that more than one patient may be monitored or provided with care through LAN 3. In addition, medical devices may be connected directly to higher-level LAN 3. For example, as shown in FIG. 1, a ventilator 6b and an anesthesia system 22 are connected directly to LAN 3, without use of a MIB. Furthermore, LAN 3 may be interconnected to a Hospital LAN backbone 4 which also is Ethernet compatible. This backbone network 4 provides communication connectivity between various departments within a hospital or medical organization; for example, connecting hospital administrative systems 15 together with laboratory system (LIS) 17. In addition, the Hospital LAN 4 has a remote access gateway 11 which provides remote, secured access from, for example, information a remote doctor's office 23 or a remote care site 24, to the various systems and devices on network 1, through for example, Internet 29. Alternatively, a remote site may also access the remote access gateway 11 directly through, for example, a dial-up telephone port, ADSL, or other types of private connection. Remote access gateway 11 may also be part of server 20, to be described below, instead of standing alone, as well know in the art.

According to the principles of the present invention, executable application 19 (or multiple applications in another embodiment) resides on central server 20 on LAN 3 for gathering and processing data from the peripheral medical devices or facilities coupled to LAN 3 or hospital LAN 4, including laboratory results supplied via laboratory system 17 connected through an HL7 interface, for example. Additional medical parameter data including additional laboratory results acquired from any number of medical devices such as those shown in FIG. 1 may be obtained by server 20 using ASTM messaging, for example. The acquired medical parameters associated with a given patient, including laboratory test results, are acquired from the medical devices on network 1 for display and control on monitors 5a, 5b or PCs 26 and 39 or any other display hosting device at any level of the FIG. 1 network. One skilled in the art can readily recognize that server 20 may reside at any level of the hierarchy of network 1, since all the different levels of LANs (e.g., 3, or 4), as well as remote sites in FIG. 1 are interconnected. An example of server 20, is a Prometheus server, marketed by Siemens Medical System. The server may be hosted, for example, by a computer system that is capable of running Microsoft NT or Windows 2000 operating system.

Figure 2:
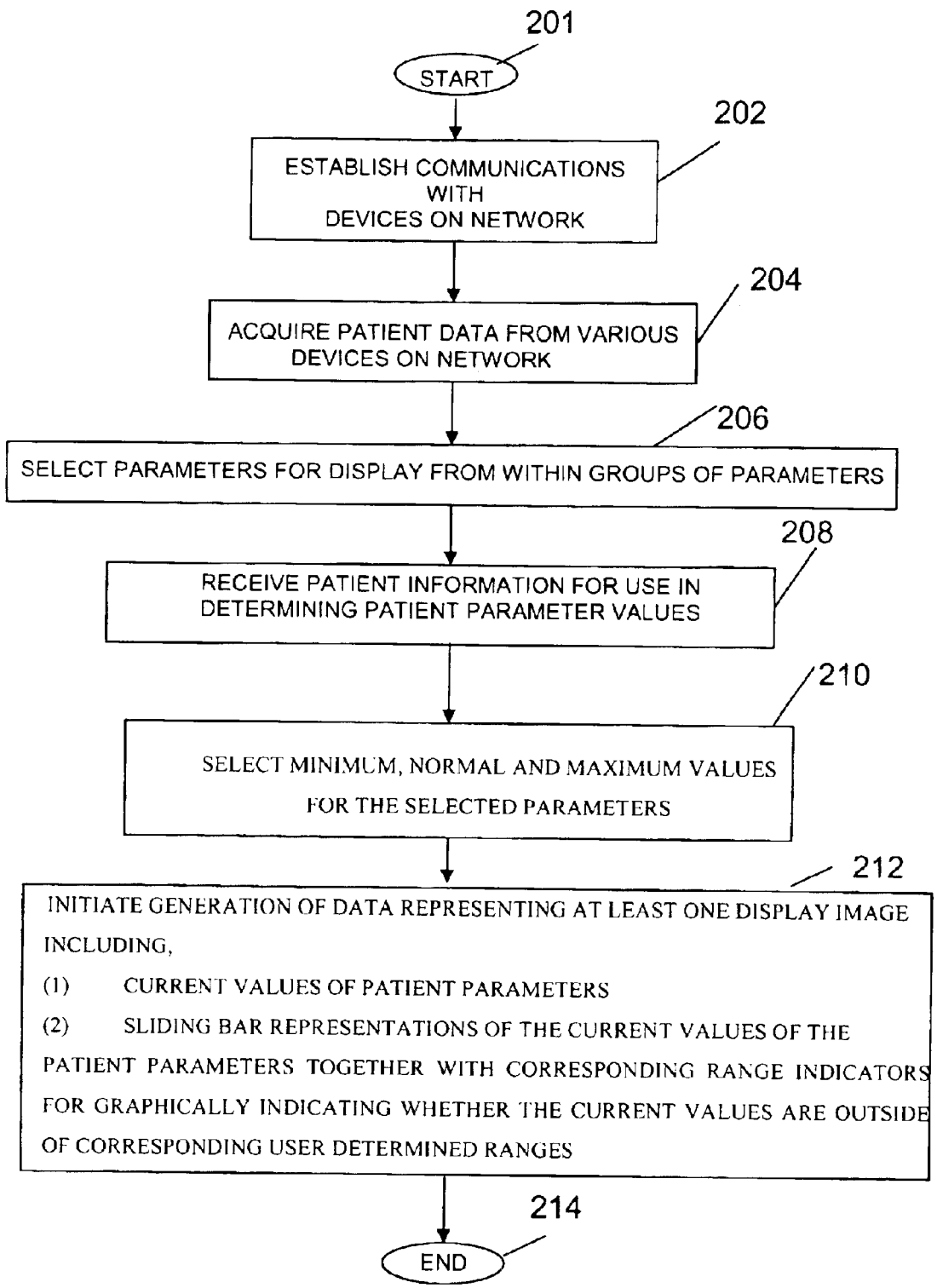
FIG. 2 represents a flowchart of a method for providing a user interface, according to the present invention.

FIG. 2 shows in flow chart form, functions that are performed by executable application 19. Application 19 establishes communication with devices on the network as shown in step 202 after the start at step 201. This is done, for example, by using IP protocol and the known IP device address for each device on the network 1 (FIG. 1), in conjunction with any higher application-layer protocols, as well known in the art. Once communication is established between server 20 and the other devices, application 19, in step 204, starts to acquire parameters that are being monitored, laboratory results and settings selected for the various devices. As previously mentioned, laboratory results may be obtained through an HL7 interface with LIS 17, or via ASTM or MIB point of care (POC) medical devices depicted in FIG. 1. Types of acquired patient parameter include, blood pressure parameters, respiratory or ventilation parameters, vital sign parameters, blood oxygen concentration representative parameters, infusion pump parameters associated with fluid delivery, drip medication related parameters and other fluid related parameters, for example.

Medical data and laboratory results may be continuously, periodically or non-periodically acquired and correlated with a given patient for storage in relational data base 25 (FIG. 1) within server 20. Data base 25 may be of the type used for storing relational data such as the Microsoft SQL server. In addition, application 19 may obtain patient parameter data and patient data comprising medical laboratory results that are first entered and stored, for example, in laboratory information system 17 of FIG. 1. Also, application 19 may acquire healthcare provider entered medical notes for display. In step 206 application 19 initiates display of a user interface configuration menu supporting user selection of patient parameters for display. The configuration menu of FIG. 4 supports user selection of multiple patient parameters from within groups of parameters including, a vascular related group of parameters 400, a respiratory related group of parameters 403 or a laboratory related group of parameters 405, for example. The parameters are individually selected from a category by check box selection as illustrated in the FIG. 4 selection table and the selected parameters are presented in a Selected Parameters window 407 for user confirmation. Application 19 in step 208 receives mass and height values entered by a user via data entry boxes 409 and 411 respectively. The received mass and height values are characteristics of the patient associated with the selected parameters. Patient weight and height are used to compute patient body surface area (BSA) used in deriving particular patient parameters such as cardiac index.

Figure 5:
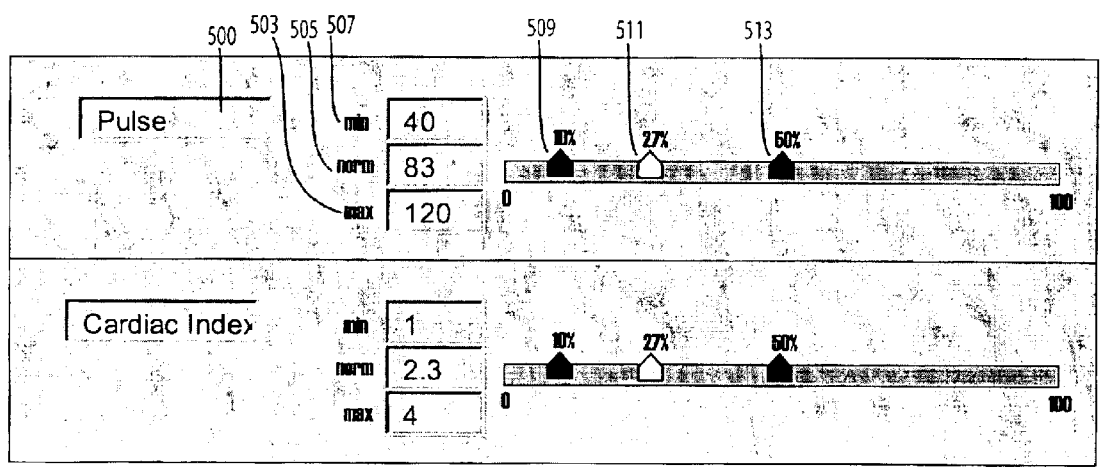

Application 19 in step 210 receives parameter information in response to user data entry via a configuration display image illustrated in FIG. 5. This figure illustrates two parameters (Pulse and Cardiac Index) for display within a user interface image. Other parameters for display in a user interface image are similarly configured using the FIG. 5 configuration display window. In operation, a user manually sets the minimum, normal, and maximum values associated with an individual patient parameter using the FIG. 5 configuration image. A user sets a minimum value 507, a normal value 505 and a maximum value 503 for a parameter (e.g., pulse) 500. A user also employs the FIG. 5 configuration display window to select parameter relative deviation ranges to be presented in a user interface image providing a display of patient vital parameters. Specifically, a user selects a normal parameter value range (indicated by blue bars in a user interface image), a cautionary range (indicated by yellow bars in a user interface image), and a non-normal range (indicated by red bars in a user interface image). A user selects ranges on a sliding bar scale as shown in FIG. 5. Specifically, a user selects a normal parameter range via blue icon 509, a cautionary parameter range via yellow icon 511 and an excessive parameter range via red icon 513 as a percentage of a maximum parameter value.

The physical interpretation of the FIG. 5 slider values is as follows. Consider, for example, patient Pulse parameter 500. A normal range of 10% implies that if a patient measurement remains within ±10% (509) of 83 beats per minute, the patient is considered as having normal heart rhythm. If the patient heart rate exceeds ±10% of the norm value but remains (in this example) within ±27% (511) of the norm value, this is shown in the user display as falling outside of the normal range but within the cautionary (yellow) range of bars. If the patient heart rate exceeds ±27% (again, in this example), the intervention range is achieved and this appears as a value between the red bars. The purpose in identifying an intervention range specific threshold value (50% (513) in this example) is so that the user, when viewing the display) advantageously has a gauge of how far a patient parameter value has deviated into this intervention range. A green bar within a user interface display image indicates a normal range. To each side of a green bar (representing a current value) are colored bars (blue, yellow, red) indicating the previously discussed ranges. Above a green bar is a current value (also shown in green) for a particular parameter. To the left of this current value is an immediately preceding value (that is, the last value measured) and to the right of the current value is the time interval between the last preceding measurement and this current value.

Figure 3:
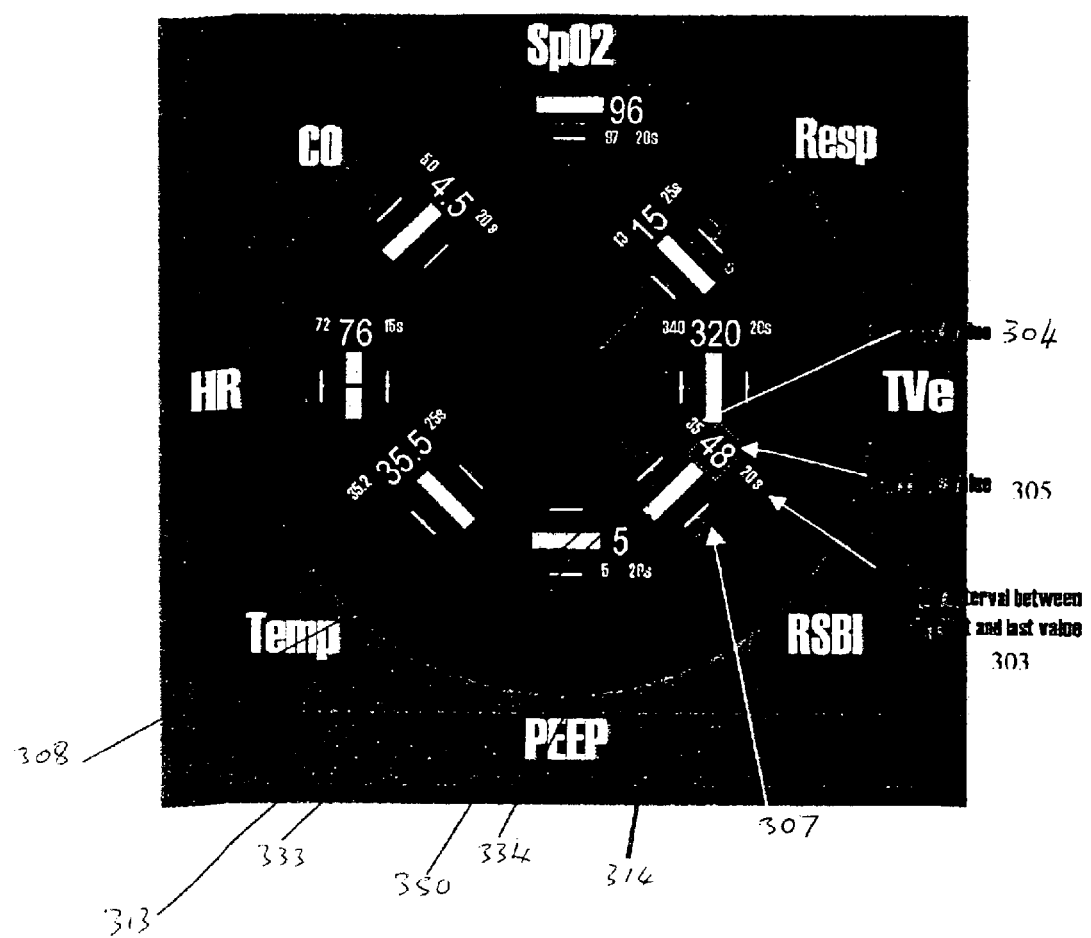
FIG. 3 shows a single user interface image presenting selected patient parameters and their acceptable ranges within the immediate eye-span of a clinician, according to invention principles.

Application 19 in step 212 employs the configuration data (entered in steps 206–210) in initiating generation of data representing at least one user interface image. An exemplary single user interface image is illustrated in FIG. 3 and presents the selected parameters and their acceptable ranges within the immediate eye-span of a clinician. In another embodiment application 19 initiates generation of data representing multiple user navigable user interface images presenting the image elements and features of FIG. 3. The user interface image of FIG. 3 includes current values of eight patient parameters including (clockwise from the top) blood oxygen saturation (SpO2), respiratory rate (Resp), spontaneous tidal volume (TVe), rapid-shallow-breathing index (RSBI), Positive end-expiratory pressure (PEEP), temperature (T), heart rate (HR) and cardiac output (CO). The user interface image includes sliding bar representations of the current values of patient parameters together with corresponding range indicators for graphically indicating whether the current values are out side of corresponding user determined ranges. A displayed sliding bar includes a current value indicator image element and a range limit identifier image element positioned at user determined positions indicative of proportions of slide bar full scale. The displayed image elements are indicated as bars in FIG. 3 but may be icons of different shape including, square, diamond, an arrow, or any other shape. Further, the displayed sliding bars employ a linear scale but in another embodiment may employ a different scale such as a logarithmic scale, for example.

The sliding bar representation for the RSBI parameter shows a current value (indicated by green bar 350, for example) together with corresponding normal, cautionary and excessive parameter range indicators. The sliding bar representation current value indicator and range limit indicators comprise image elements having a common display attribute when the current value is within a corresponding range limit. The image element common display attribute comprises a particular image element color in the embodiment of FIG. 3 but in other embodiments may comprise, a particular image element shape, a particular image element type of highlighting, a particular image element foreground or background, a particular type of image element shading, a particular image element outline or a particular image element fill pattern, for example.

The corresponding normal range indicators comprise blue bars 333 and 334, the cautionary range indicators comprise yellow bars 313 and 314 and the excessive parameter range indicators comprise red bars 307 and 308. The sliding bar representation graphically indicates where current value 350 resides within these ranges and the RSBI parameter current value 350 is shown lying within the normal range blue bars for example. If the current value exceeds the cautionary range, the current value indicator color is yellow and if the current value lies in the excessive range, the current value indicator is red. Thereby, in the exemplary embodiments of FIG. 3 and FIGS. 6–8) the current value and range limit indicator image elements have a common color when the current value is within a corresponding range limit.

The patient parameter current values and associated sliding bar representations of the patient parameters are oriented in a rotational orientation but in other embodiments may be in a horizontal, vertical or spiral orientation, for example. Further, individual current values and associated sliding bar representations of individual patient parameters are advantageously ordered by type of associated patient parameter so that patient parameters that typically exhibit out of range conditions together are adjacent in a single display image. The user interface image also presents a numerical value 305 corresponding to the patient parameter current value indicated in the RSBI sliding bar by green bar 350, for example. Patient parameter current value 305 is accompanied by the patient parameter numerical value 304 received prior to this current parameter value, as well as a numerical time interval 303 substantially indicative of time between measurement of the current parameter value 305 and the previously received parameter value 304. The user interface image also presents a patient parameter label (e.g., RSBI).

Figure 6:
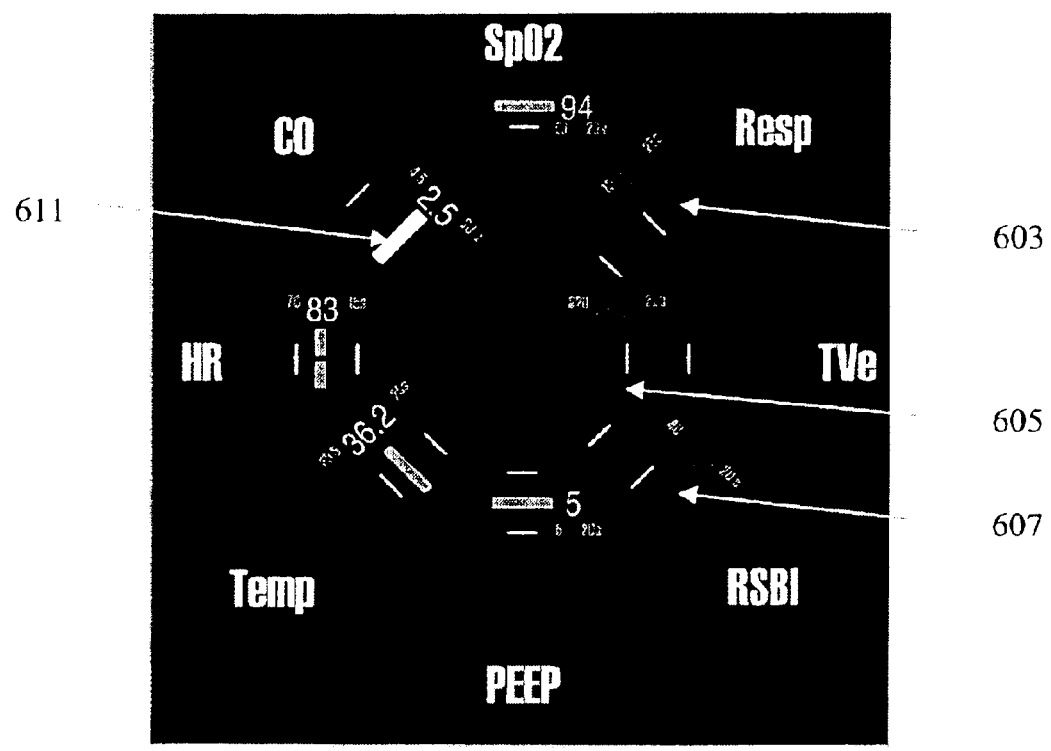
FIGS. 6 and 7 show further user interface images presenting selected patient parameters, according to invention principles.

FIG. 6 show the user interface display image of FIG. 3 illustrating particular parameters exceeding their normal value ranges. FIG. 6 shows several parameters (respiratory rate—Resp, tidal volume—TVe, and rapid shallow breathing index—RSBI) that are deviating significantly from their normal values. Specifically, the sliding bar current value indicators for these parameters (603, 605 and 607) are red and positioned in the excessive ranges of these parameters. This advantageously distinguishes the excessive parameter values from the other parameter values and readily signals to a user that medical intervention is required. In addition, in the FIG. 6 user interface image, the cardiac output parameter value is shown deviating into the cautionary range. The sliding bar current value indicator for the cardiac output parameter (611) is shown in yellow and is positioned in the cautionary range of this parameter. This advantageously distinguishes the parameter value in the cautionary range from the excessive parameter values and from the other parameter values in the normal range.

Figure 7:
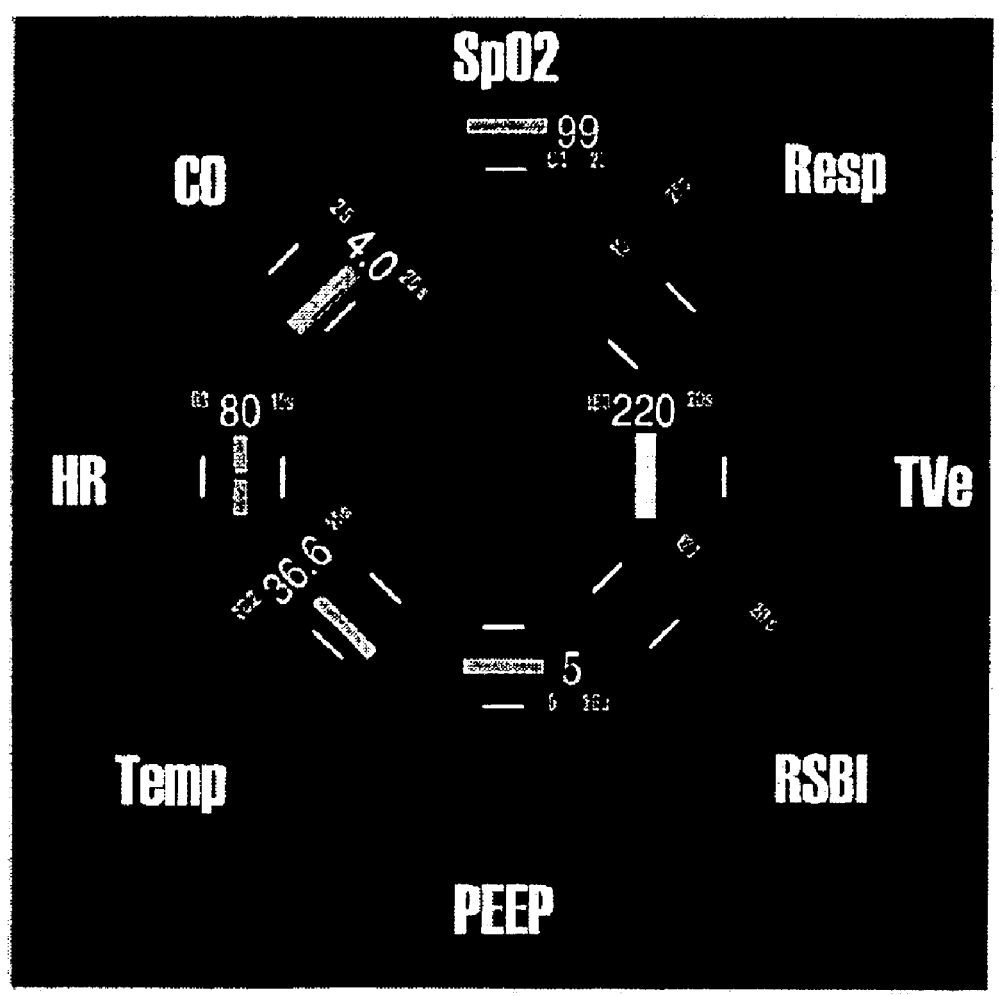

FIG. 7 shows the user interface display image of FIG. 6 with the CO parameter back in the normal range and the TVe parameter back into the cautionary range from the excessive range. The user interface system shows the selected patient parameter data that enables a user to rapidly determine the state of health of a patient within the span of a single glance. A user interface image shows selected patient parameter data together with previous values enabling rapid comparison of a patient parameter value with an immediate pre-cursor value and also enabling rapid relative comparison of different vital sign parameters and their associated range categorized deviation. Such rapid comparison is facilitated by the association of particular display attributes (such as different colors) with different parameter variation ranges indicating deviation from a normal range. In the embodiment of FIGS.

3, 6 and 7 parameter range deviation is indicated by a patient parameter current value indicator that traverses a sliding bar between user determined minimum and maximum values and the sliding bar lies along a single axis. The single axis is either horizontal or at an angle from the horizontal for the displayed parameters. In other embodiments the sliding bar representation may comprise a curved bar, a rotary bar or a bar along a plurality of axes, for example.

The user interface system and associated configuration display images, is Web-based in the preferred embodiment (but in other embodiments is compatible with any network environment) and operates through a thin-client viewer (such as MS Internet Explorer or equivalent). The applications that create the user views are, for example, based on ActiveX components consisting of Java Applets, JavaScript, and JSPs, but in other embodiments may be based on any applicable programming instruction code. A user may use a Microsoft Windows compatible PC 26 or Windows NT compatible PC 39 as shown in FIG. 1, or any other processing devices capable of running a menu generating program such as a web browser program (e.g., Microsoft Internet Explorer or Netscape Navigator, etc.) to view a user interface image such as those of FIGS. 3, 6 and 7. Further the user interface system may also generate a composite display image including such a user interface image together with medical parameters and laboratory results information associated with a given patient.

A user may use a web browser on any processing device, as long as a communication connection can be made to server 20 and application 19, to make requests and view information acquired and stored in data base 25. This is advantageous, since a doctor may for example, gain access to data base 25 or laboratory test results from, for example, a remote physician's office 23, without having to access a dedicated terminal. Of course, a user can simply use a keyboard and/or a mouse or any other user interface devices to enter a user selection or request on a user computer, as is known in the art. Application 19 is therefore capable of collating and formatting medical data to be compatible with, for example, HTML (Hypertext Mark-up Language) programming language for displaying data on a web browser. Application 19 is also responsive to, for example, HTTP (HyperText Transfer Protocol) commands originated from a user's web browser for making a request. The process of FIG. 2 ends at step 214.

Figure 8:
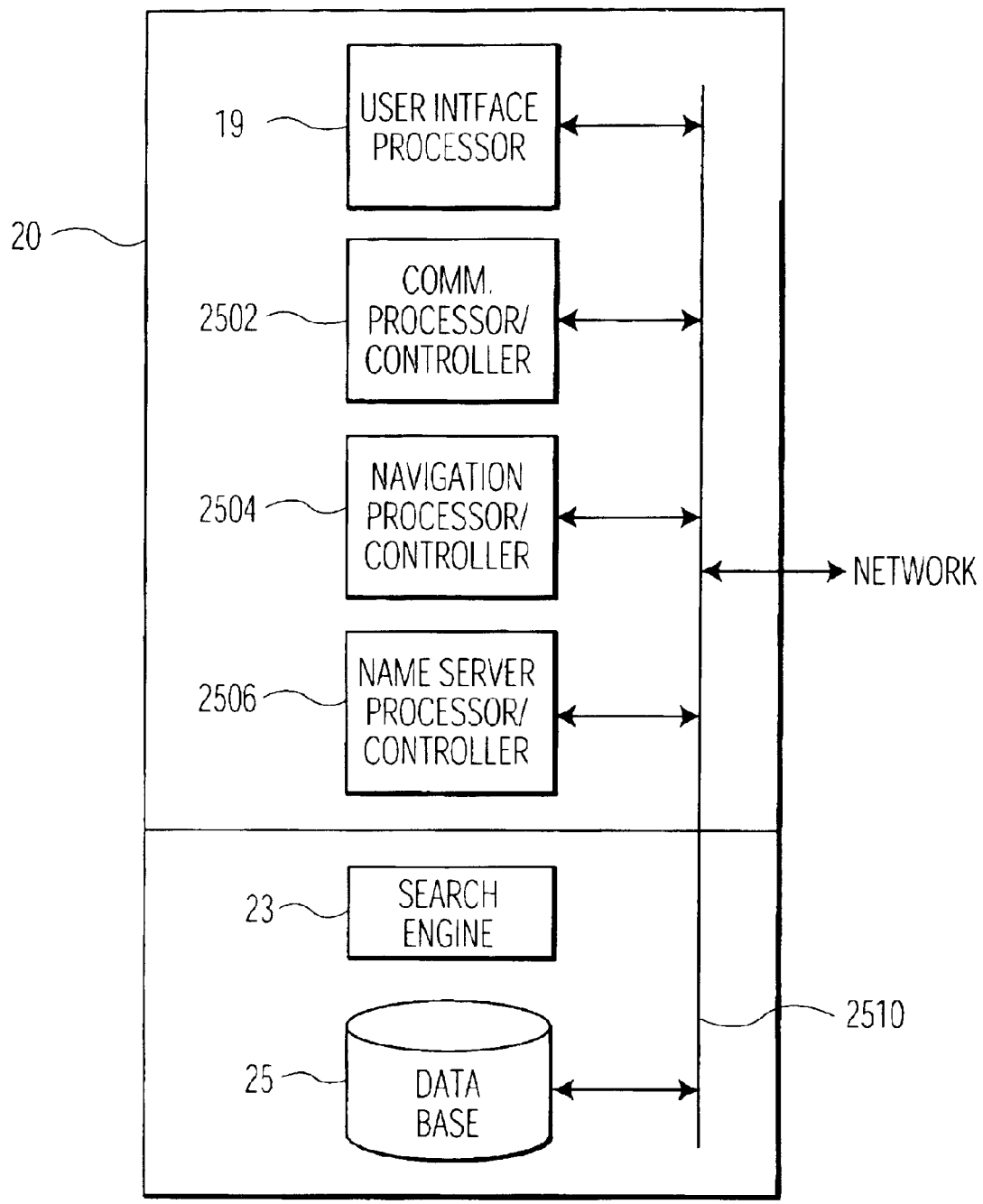
FIG. 8 is a block diagram of a server having functionality in accordance with the present invention.
Figure 1:
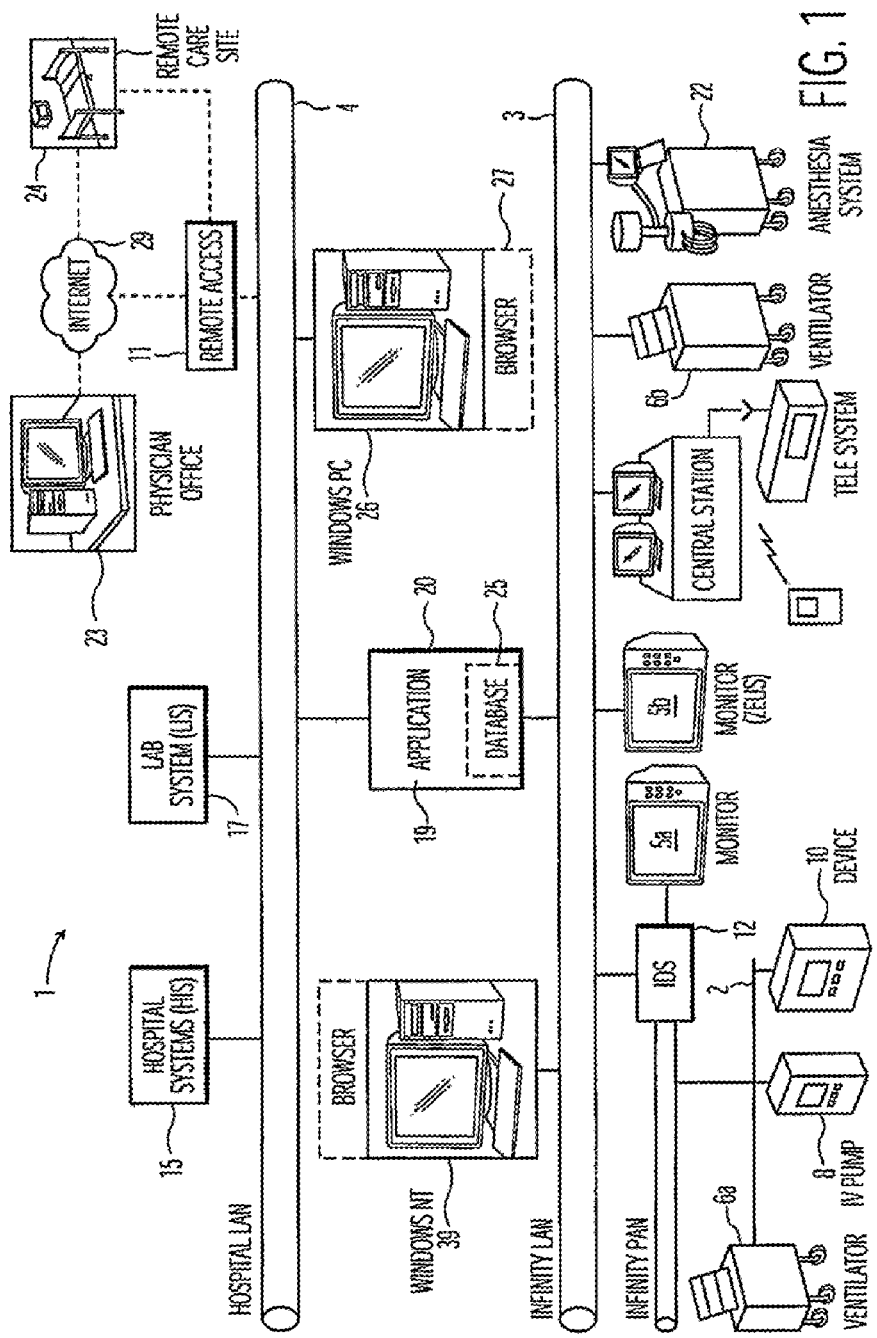
Figure 2:
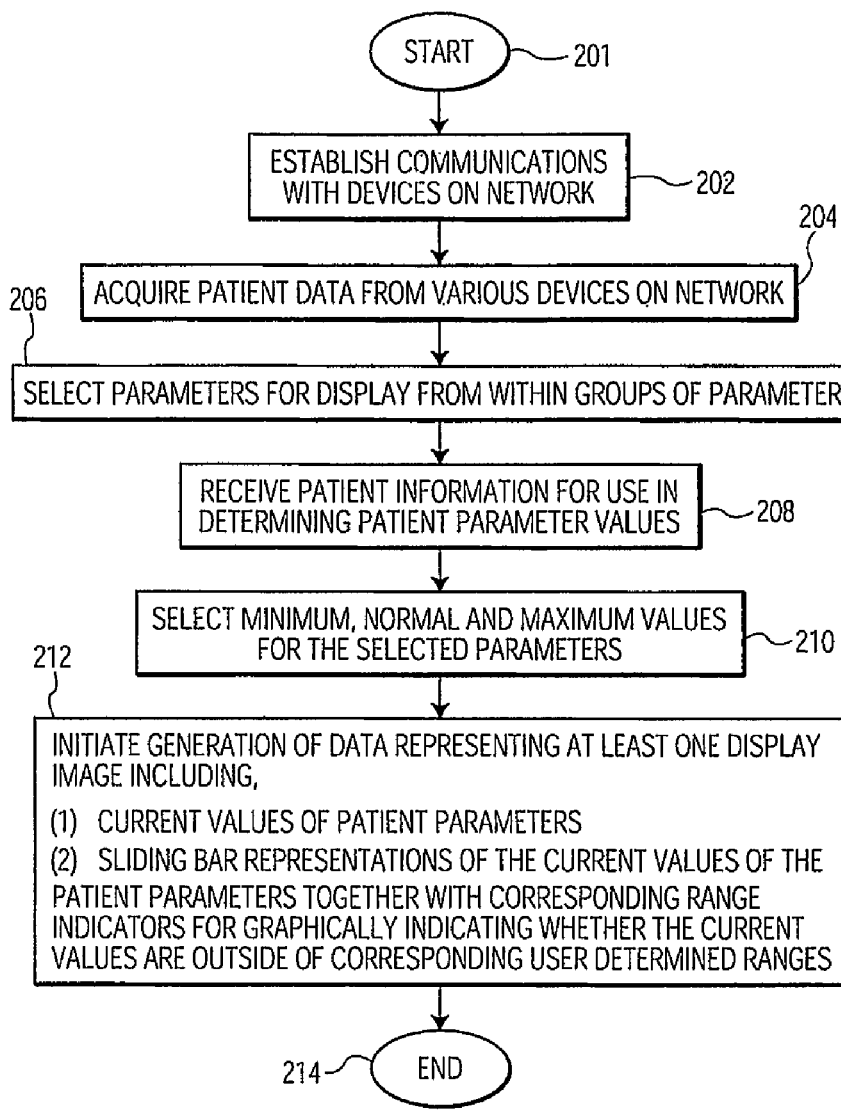
Figure 3:
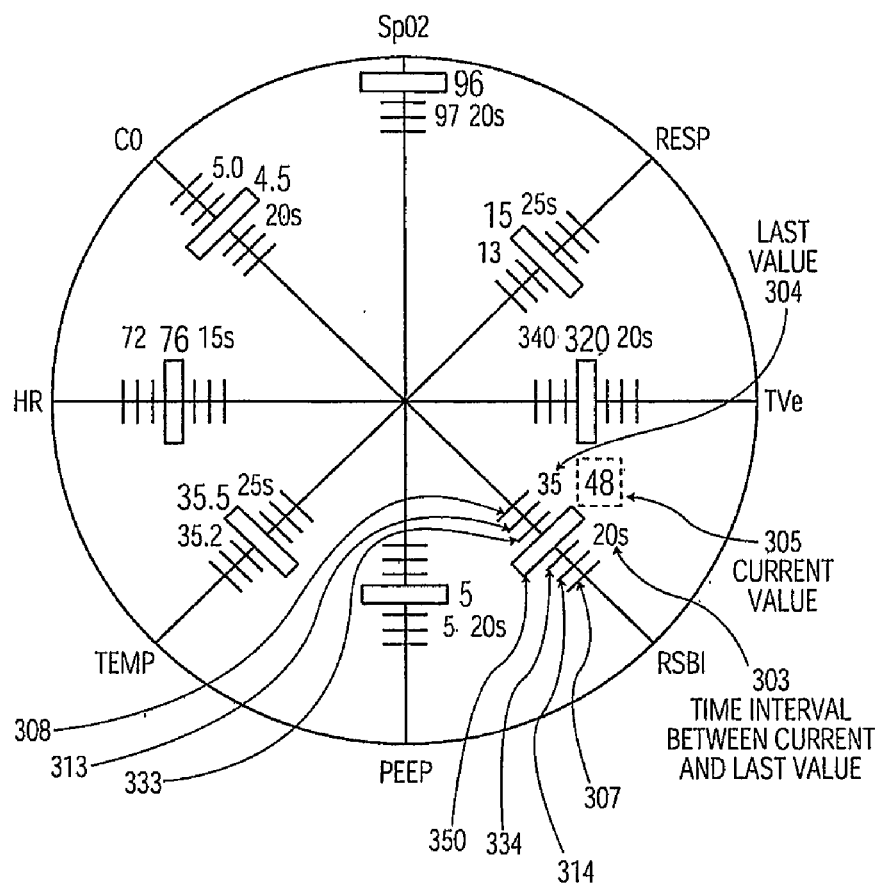
Figure 5:
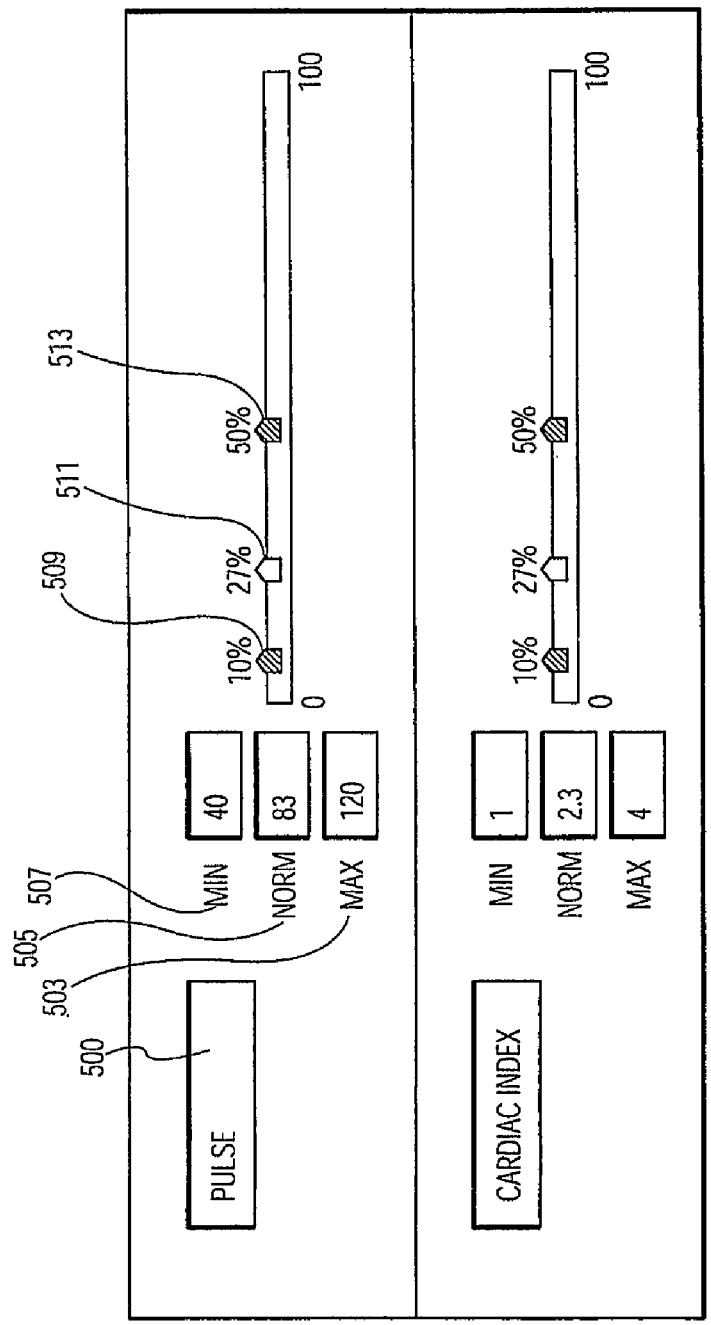
Figure 6:
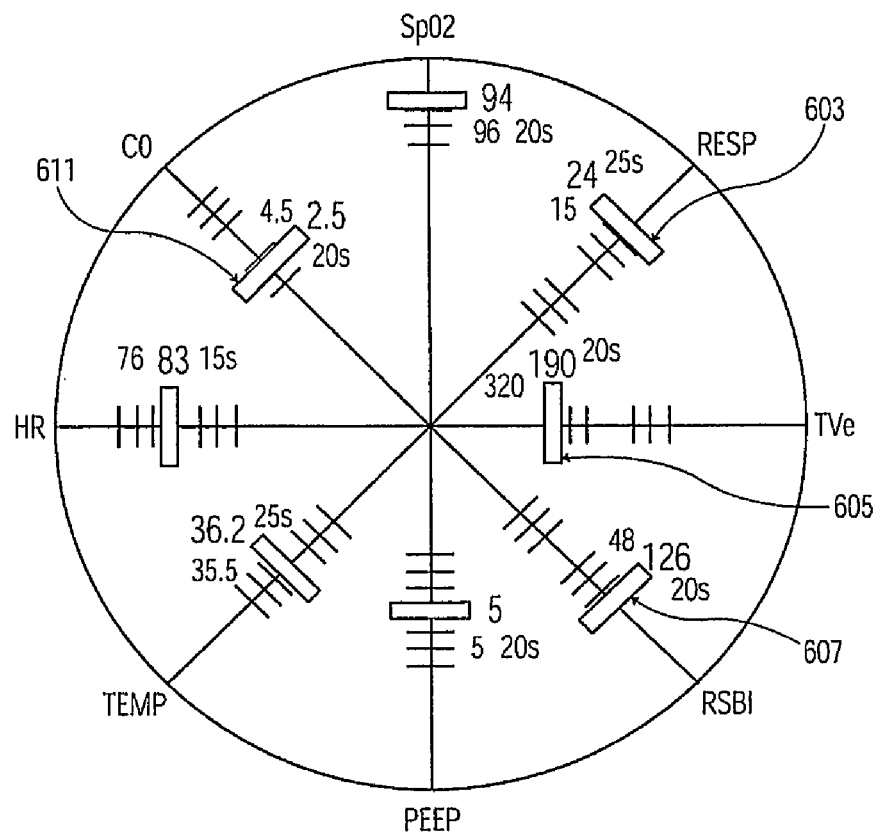
Figure 7:
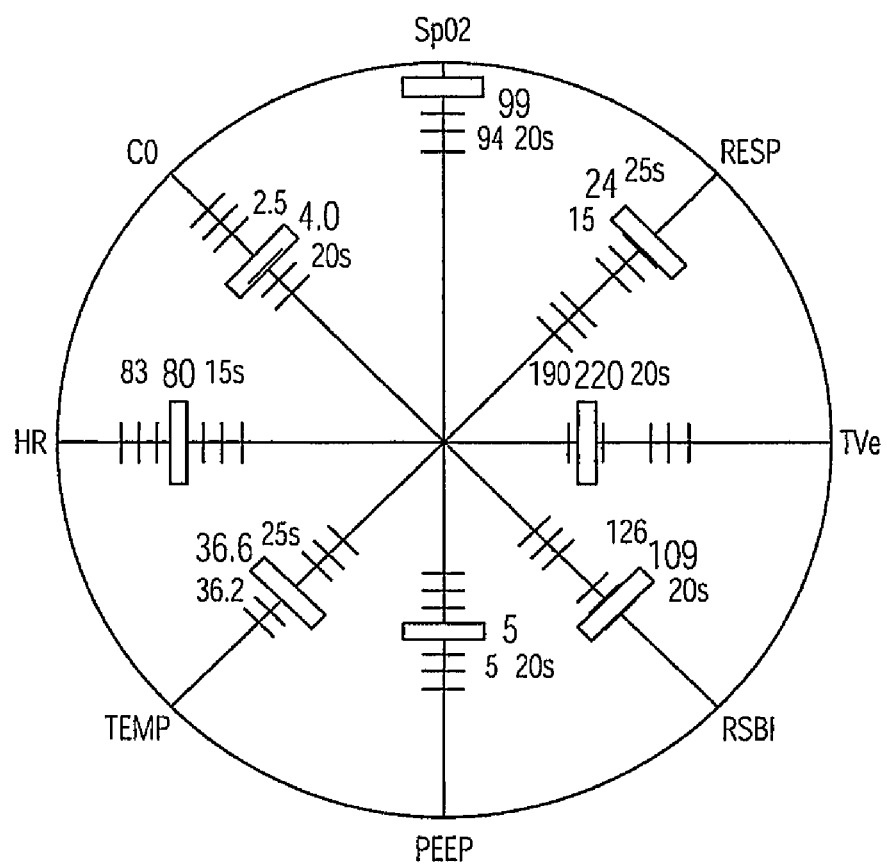
Figure 8:
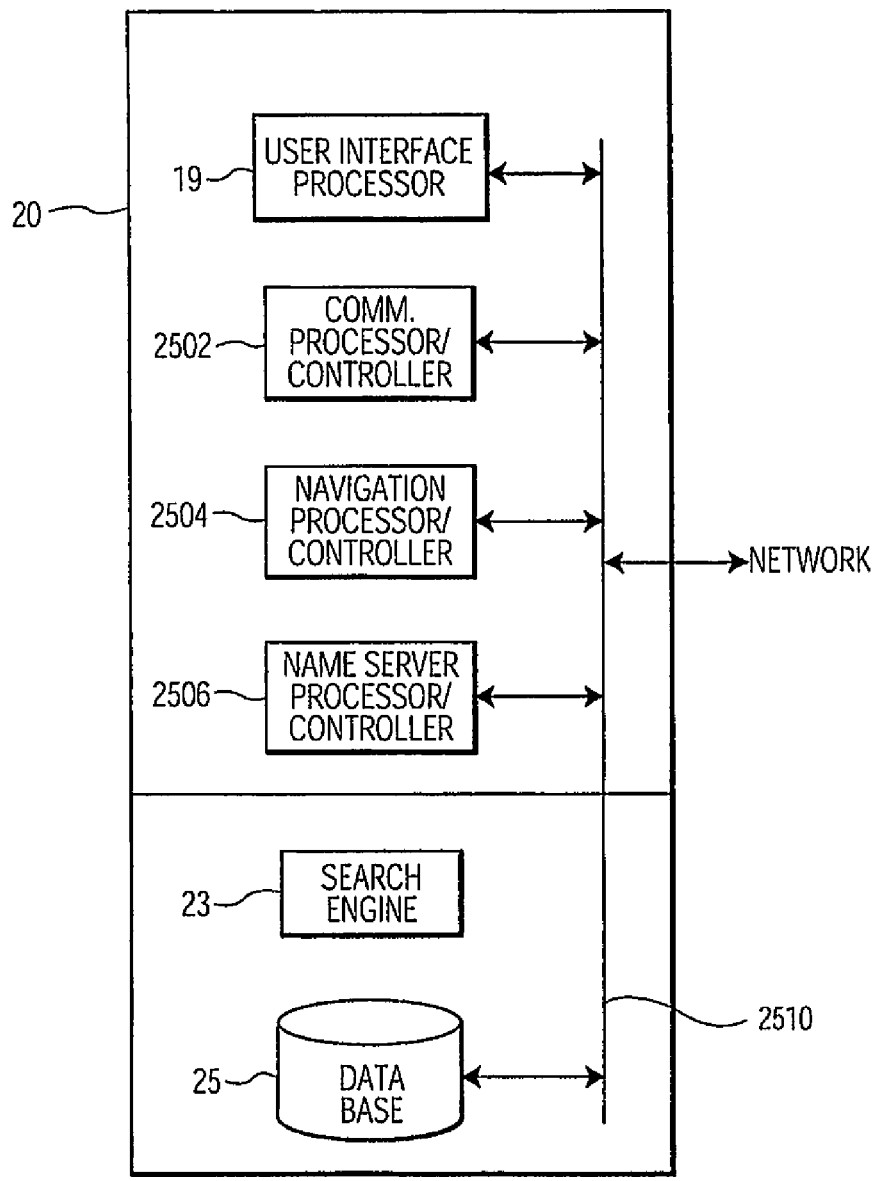

FIG. 8 shows a block diagram of an exemplary embodiment of server 20 (FIG. 1) including functions in accordance with the present invention for generating data for configuring and presenting a user interface display according to invention principles and for managing, collating, searching and updating data base 25 containing patient medical information. Executable applications or processors operative to carry out instructions for performing the various functions described herein include an executable application 19 for performing user interface related processing and communications processing module 2502 that acquires the patient data including the monitored parameters allocated to a given patient from the network and collates the information for storage in data base 25. Navigation collation processor 2504 operates in conjunction with the web browser and display generator software to collate and prioritize parameters for display to the user while navigating through various applications selected by a user through the user interface. Name server processor 2506 associates unique identifiers (IDs) with each node connected to the system network and with each patient in the system in order to track and update patient information throughout the system. Input/output data and control signals are used to communicate between the various processors as well as to interface with the data base 25 and search engine 23 and with the network via communication line 2510.

The user interface display images, systems and processes presented in FIGS. 1–8 are not exclusive. Other user interface configuration and presentation display images, systems and processes may be derived in accordance with the principles of the invention to accomplish the same objectives. Although this invention has been described with reference to particular embodiments, it is to be understood that the embodiments and variations shown and described herein are for illustration only and that various modifications may be implemented by those skilled in the art without departing from the scope of the invention. A user interface system and associated functions according to the invention may be used in any application to support user viewing of substantially real-time data and to enable data comparison in the span of a user glance.

What is claimed is:

1. A system for providing a user interface presenting a plurality of patient medical parameters, comprising:

an acquisition processor for acquiring, from a patient monitoring device, data representing a plurality of patient parameters; and a processor for initiating generation of data representing a single display image including, (a) a plurality of current values of said plurality of patient parameters and (b) a sliding bar representation of each of said plurality of current values of said plurality of patient parameters together with corresponding range indicators for graphically indicating whether each of said current values is outside of a corresponding user determined range wherein said range indicators correspond to a plurality of different value ranges individually having range limit identifiers with a common visual display attribute with a current value indicator image element when said current value is within an individual range and said current value indicator image element having a second visual display attribute different from said first visual display attribute when said current value is outside said individual range.

2. A system according to claim 1, wherein said image element common display attribute comprises a particular image element color.

3. A system according to claim 2, wherein said image element common display attribute comprises at least one of, (a) a particular image element fill pattern, (b) a particular image element shape, (c) a particular image element type of highlighting, (d) a particular image element foreground or background, (e) a particular type of image element shading, and (f) a particular image element outline.

4. A system according to claim 1, wherein said sliding bar representation user determined range includes at least two of, (a) a normal range indicator, (b) a cautionary range indicator and (c) an excessive range indicator and graphically indicates where said current value is within a range.

5. A system according to claim 1, wherein said sliding bar representation includes a current value indicator image element and a plurality of range limit identifier image elements corresponding to a plurality of value ranges and an individual range limit identifier has a common display attribute with said current value indicator image element when said current value is within said individual range.

6. A system according to claim 5, wherein said plurality of ranges comprise at least two of, (i) a normal range, (ii) a cautionary range and (iii) an excessive range and said image element common display attribute comprises at least one of, (a) a particular image element color, a particular image element shape, (c) a particular image element type of highlighting, (d) a particular image element foreground or background, (e) a particular type of image element shading, (f) a particular image element outline, and (g) a particular image element fill pattern.

7. A system according to claim 1, wherein said single display image includes at least one of, (a) a value of said patient parameter received prior to said current parameter value, (b) a normal value of said patient parameter, (c) a time interval substantially indicative of time between measurement of said current parameter value and a previously received parameter value, (d) a patient parameter label.

8. A system according to claim 7, wherein a patient parameter label has a common display attribute with another different patient parameter label, said display attribute comprising at least one of, (a) a particular image element color, (b) a particular image element shape, (c) a particular image element type of highlighting, (d) a particular image element foreground or background, (e) a particular type of image element shading, (f) a particular image element outline, and (g) a particular image element fill pattern.

9. A user interface system according to claim 1, wherein said patient parameter comprises at least one of, (a) a blood pressure parameter, (b) a ventilation parameter, (c) a vital sign parameter, (d) a blood concentration representative parameter, (e) a spontaneous tidal volume parameter, (f) a respiratory rate parameter, (g) a positive end-expiratory pressure parameter, (h) a temperature, (i) a heart rate, (j) a cardiac output, (k) an infusion pump parameter associated with fluid delivery, (l) a drip medication related parameter and (m) another fluid related parameter.

10. A system according to claim 1, wherein said single display image includes a plurality of individual current values and associated sliding bar representations of individual patient parameter oriented in said single display image in a rotational orientation; and said sliding bar representation represents at least one of, (a) a linear scale, (b) a logarithmic scale.

11. A system according to claim 10, wherein said single display includes a plurality of individual current values and individual current values and associated sliding bar representations of individual patient parameters are oriented in said single display image in at least one of, (a) a horizontal orientation and (b) a vertical orientation; and said sliding bar representation includes a current value indicator image element and a range limit identifier image element positioned at user determined positions indicative of proportions of slide bar full scale.

12. A system according to claim 1, wherein said sliding bar representation comprises at least one of, (a) a bar along a single axis, (b) a bar along an axis at an angle from horizontal, (c) a curved bar, (d) rotary bar and (e) a bar along a plurality of axes.

13. A system for providing a user interface presenting a plurality of patient medical parameters, comprising:

an acquisition processor for acquiring, from a patient monitoring device, data representing a plurality of patient parameters;

a processor for initiating generation of data representing a single display image including,
(a) a plurality of current values of a plurality of patient parameters and
(b) sliding bar representations of said plurality of current values of said plurality of patient parameters together with corresponding range indicators for graphically indicating whether said current values are outside of corresponding user determined ranges and (i) said range indicators correspond to a plurality of different value ranges individually having range limit identifiers with a common display attribute with a current value indicator image element when said current value is within an individual range; and wherein individual current values and associated sliding bar representations of individual patient parameters are ordered by type of associated patient parameter so that patient parameters that typically exhibit out of range conditions together are adjacent in said single display image.

14. A system according to claim 13, wherein said plurality of different value ranges comprise at least two of, (i) a normal range, (ii) a cautionary range and (iii) an excessive range and individual current values and associated sliding bar representations of individual patient parameters are oriented in said single display image in a rotational orientation.

15. A system according to claim 13, wherein said plurality of patient parameters are selected from within groups of parameters including at least one of, (a) a vascular related group of parameters, (b) a respiratory related group of parameters and (c) a laboratory related group of parameters.

16. A system according to claim 15, wherein said processor receives patient mass and height information for use in computing body surface area and cardiac index.

17. A system for configuring a user interface display image for presenting patient medical parameter data, comprising:

a processor for initiating generation of data representing a single display image including, a linear sliding bar representation of a patient parameter value permitting user selection of a range limit identifier image element at a position indicative of a proportion of slide bar full scale, said range limit identifier image element being for use in a patient parameter display image for graphically indicating whether a patient parameter current value is outside of a user determined range and said sliding bar representation of said patient parameter current value is presented together with corresponding range indicators for graphically indicating whether said patient parameter current value is outside of a plurality of corresponding different user determined ranges and said range indicators correspond to a plurality of value ranges individually having range limit identifiers with a common display attribute with a current value indicator image element when said current value is within an individual range.

18. A system according to claim 17, wherein said plurality of corresponding different user determined ranges comprise at least two of, (a) a normal range, (b) a cautionary range and (c) an excessive range and graphically indicates where said current value is within a range.

19. A system according to claim 17, wherein said at least one display image includes data entry boxes enabling a user to enter at least one of, (a) a minimum parameter value, (b) a normal parameter value and (c) a maximum parameter value.

20. The system according to claim 1, wherein said plurality of current values of a plurality of patient parameters are displayed in a circular pattern representation enabling the user to more easily discern and detect changes and alarm situations.

21. The system according to claim 13, wherein said plurality of current values of a plurality of patient parameters are displayed in a circular pattern representation enabling the user to more easily discern and detect changes and alarm situations.

* * * * *

UNITED STATES PATENT AND TRADEMARK OFFICE
CERTIFICATE OF CORRECTION

PATENT NO. : 6,956,572 B2
APPLICATION NO. : 10/616219
DATED : Ocotber 18, 2005
INVENTOR(S) : John R. Zaleski It is certified that error appears in the above-identified patent and that said Letters Patent is hereby corrected as shown below:

The title page should be deleted and substitute therefor the attached title page.
Please replace informal drawings with the attached formal drawings.

Signed and Sealed this

Thirtieth Day of October, 2007

JON W. DUDAS
*Director of the United States Patent and Trademark Office*

(12) United States Patent
Zaleski

(10) Patent No.: US 6,956,572 B2
(45) Date of Patent: Oct. 18, 2005

(54) PATIENT MEDICAL PARAMETER USER INTERFACE SYSTEM

(75) Inventor: John R. Zaleski, West Brandywine, PA (US)

(73) Assignee: Siemens Medical Solutions Health Services Corporation, Malvern, PA (US)

(*) Notice: Subject to any disclaimer, the term of this patent is extended or adjusted under 35 U.S.C. 154(b) by 66 days.

(21) Appl. No.: 10/616,219

(22) Filed: Jul. 8, 2003

(65) Prior Publication Data
US 2004/0158132 A1 Aug. 12, 2004

Related U.S. Application Data
(60) Provisional application No. 60/446,313, filed on Feb. 10, 2003.

(51) Int. Cl.$^7$ .................. G09G 5/22; A61B 5/00
(52) U.S. Cl. .................. 345/440.2; 600/300
(58) Field of Search .................. 345/440, 440.1, 345/440.2, 700, 762, 764, 883; 600/300, 301

(56) References Cited

U.S. PATENT DOCUMENTS

| | | | |
|---|---|---|---|
| 5,482,050 A | 1/1996 | Smokoff et al. | 128/710 |
| 5,915,379 A * | 6/1999 | Wallace et al. | 128/204.21 |
| 6,095,984 A | 8/2000 | Amano et al. | |
| 6,174,283 B1 | 1/2001 | Nevo et al. | 600/301 |
| 6,188,407 B1 | 2/2001 | Smith et al. | 345/353 |
| 6,289,812 B1 | 8/2001 | Wallace et al. | 128/205.23 |
| 6,287,452 B1 | 9/2001 | Allen et al. | |
| 6,369,838 B1 | 4/2002 | Wallace et al. | 345/810 |
| 6,429,869 B1 * | 8/2002 | Kamakura et al. | 345/440.2 |
| 2002/0015034 A1 | 2/2002 | Malmborg et al. | 345/204 |
| 2002/0077853 A1 | 6/2002 | Rutledge et al. | 705/3 |
| 2002/0082857 A1 | 6/2002 | MacCarter et al. | 705/2 |
| 2002/0183976 A1 | 12/2002 | Pearce | 702/188 |
| 2003/0037786 A1 * | 2/2003 | Biondi et al. | 128/204.21 |
| 2003/0092974 A1 | 5/2003 | Santoso et al. | 600/300 |
| 2003/0095147 A1 | 5/2003 | Daw | 345/771 |
| 2004/0116834 A1 * | 6/2004 | Mostafavi | 600/428 |

FOREIGN PATENT DOCUMENTS

DE 198 44 918 A1 9/1998

* cited by examiner

*Primary Examiner*—Matthew Luu
(74) *Attorney, Agent, or Firm*—Alexander J. Burke, Esq.

(57) ABSTRACT

A user interface enables a critical care clinician (such as a respiratory therapist, nurse, resident, or attending physician) to quickly ascertain a patient condition as part of a patient care management procedure. A system according to invention principles comprises a user interface display providing a quick and convenient way to display key vital parameters and their acceptable ranges within the immediate eye-span of a clinician. A system provides a user interface presenting patient medical parameter data, and includes an acquisition processor for acquiring, from a patient monitoring device, data representing a patient parameter. The system includes a processor for initiating generation of data representing at least one display image including, (a) a current value of a patient parameter and (b) a sliding bar representation of the patient parameter current value together with a range indicator for graphically indicating whether the current value is outside of a user determined range.

21 Claims, 8 Drawing Sheets

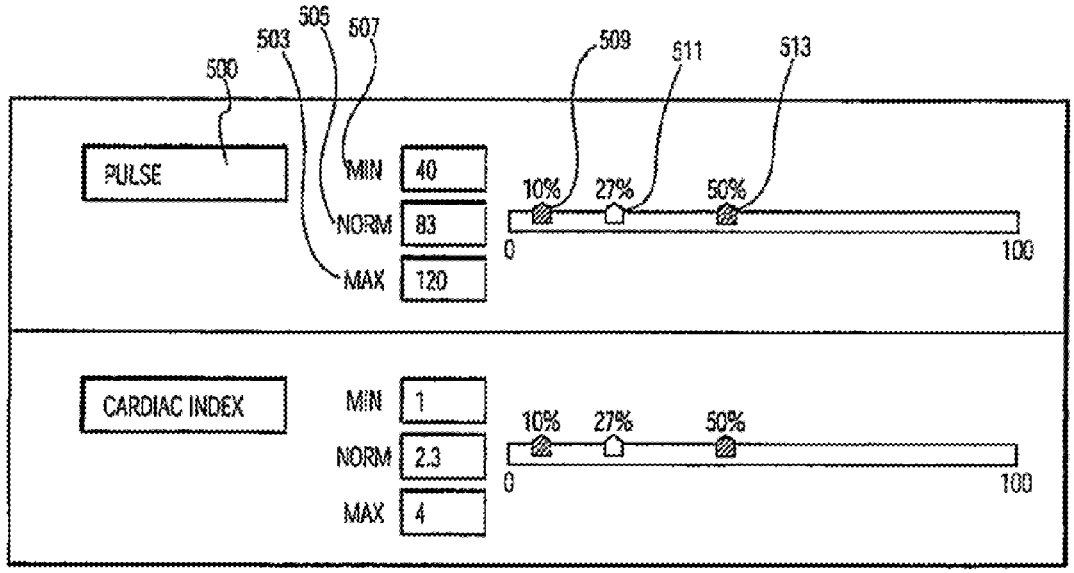

| VASCULAR 400 | | RESPIRATORY 403 | | LABORATORY 405 | |
|---|---|---|---|---|---|
| ☑ | PULSE | ☑ | RESP RATE | ☐ | HEMOGLOBIN |
| ☐ | CARDIAC INDEX | ☑ | TIDAL VOLUME | ☐ | K |
| ☑ | CARDIAC OUTPUT | ☐ | MINUTE VOLUME | ☐ | Ca |
| ☑ | O2 SATURATION | ☑ | PEEP | ☐ | SaO2 |
| ☑ | CORE TEMP | ☑ | RSBI | ☐ | PO2 |
| ☐ | PAP | ☐ | IMV LEVEL | ☐ | PCO2 |
| ☐ | CVP | ☐ | DYN. COMPL. | ☐ | pH |
| ☐ | | ☐ | | ☐ | |

SELECTED PARAMETERS 407

PULSE CARDIAC
OUTPUT O2
SATURATION
TEMPERATURE RR
TVe CARDIAC INDEX
CARDIAC INDEX

409 MASS (kg) 53
411 HEIGHT (cm) 145

FIG. 4